(12) United States Patent  (10) Patent No.: US 8,115,028 B2
Ennis et al.  (45) Date of Patent: Feb. 14, 2012

(54) SHORTENED SYNTHESIS USING PARAFORMALDEHYDE OR TRIOXANE

(76) Inventors: Seth C. Ennis, Limerick (IE); Cornelia Fuchs, Krefeld (DE); Ralf Kanzler, Leverkusen (DE); Dean A. Johnson, Kent (GB)

( * ) Notice: Subject to any disclaimer, the term of this patent is extended or adjusted under 35 U.S.C. 154(b) by 331 days.

(21) Appl. No.: 12/304,008

(22) PCT Filed: Jun. 5, 2007

(86) PCT No.: PCT/EP2007/004976
§ 371 (c)(1),
(2), (4) Date: Dec. 9, 2008

(87) PCT Pub. No.: WO2007/144091
PCT Pub. Date: Dec. 21, 2007

(65) Prior Publication Data
US 2010/0292499 A1 Nov. 18, 2010

(30) Foreign Application Priority Data

Jun. 12, 2006 (EP) .................................. 06012053
Jun. 12, 2006 (IE) .................................. S2006/0435

(51) Int. Cl.
*C07C 69/035* (2006.01)
(52) U.S. Cl. ...................................................... 560/140
(58) Field of Classification Search .................. None
See application file for complete search history.

(56) References Cited

U.S. PATENT DOCUMENTS 3,509,180 A * 4/1970 Elliott ............................. 549/497
6,713,464 B1 3/2004 Meese et al.
6,858,650 B1 2/2005 Meese

FOREIGN PATENT DOCUMENTS

| EP | 1582523 | 10/2005 |
| WO | 94/11337 | 5/1994 |
| WO | 99/58478 | 11/1999 |
| WO | 01/35957 | 5/2001 |

OTHER PUBLICATIONS

Greene, Protective Groups in Organic Chemistry, 1981, John Wiley & Sons, Inc, New York, pp. 29-31.*

* cited by examiner

Primary Examiner — Paul A Zucker
(74) Attorney, Agent, or Firm — Kenyon & Kenyon LLP

(57) ABSTRACT

The present disclosure relates to a process for the preparation of a compound of formula (I) wherein R is hydrogen, a formyl group, a straight, branched or cyclic $C_1$-$C_6$ alkylcarbonyl group or a phenylcarbonyl group, or a salt thereof, characterized by the steps of reacting a compound of formula (II) with a mixture of Grignard initiator and Mg in a solvent to form a Grignard reagent, reacting the Grignard reagent with paraformaldehyde or trioxane to obtain a compound of formula (III) and then further reacting the compound of formula (III) in a known manner to obtain a compound of formula (I) and optionally salt formation.

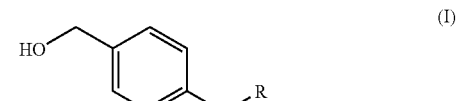

(I)

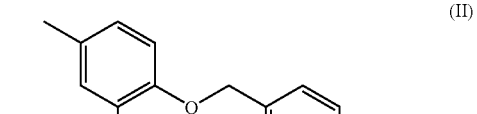

(II)

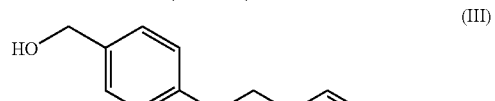

(III)

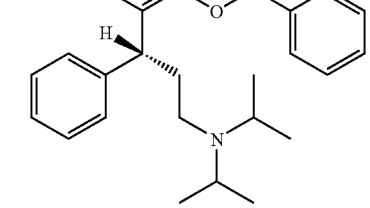

28 Claims, No Drawings

SHORTENED SYNTHESIS USING PARAFORMALDEHYDE OR TRIOXANE

CROSS REFERENCE TO RELATED APPLICATION

This application is a 371 of International Patent Application No. PCT/EP2007/004976, filed Jun. 5, 2007, which claims priority to European Patent Application No. 06012053.2, filed Jun. 12, 2006, and Irish Patent Application No. S2006/0435, filed Jun. 12, 2006. The contents of these applications are hereby incorporated by reference in their entireties.

TECHNICAL FIELD

Presently described is a process for the preparation of 2-(3-diisopropylamino-1-phenylpropyl)-4-(hydroxymethyl) phenol which is known as the active metabolite of tolterodine (hereafter referred to as the "Active Metabolite") and its phenolic monoesters by a shortened synthetic route via a Grignard reaction. The target compounds have the following formula (I):

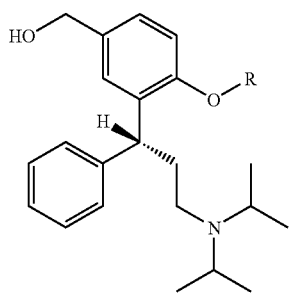

(I)

wherein R is hydrogen, formyl, a straight, branched or cyclic $C_1$-$C_6$ alkylcarbonyl group or a phenylcarbonyl group. If R in formula (I) is hydrogen, the formula represents the Active Metabolite.

A particular preferred example of the phenolic monoesters of formula (I) is Fesoterodine which can be chemically defined as R-(+)-Isobutyric acid 2-(3-diisopropylamino-1-phenylpropyl)-4-(hydroxymethyl)phenol ester. Fesoterodine is represented by the formula (Ia) depicted below.

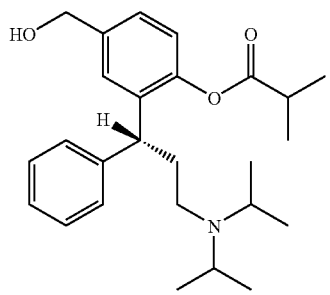

(Ia)

Compounds of formula (I) including the Active Metabolite and its phenolic monoesters of formula (I) are known from WO 99/058478.

Also described herein is a process for the preparation of salts of the compounds of formula (I), specifically including the preparation of salts of Fesoterodine, and more particularly the preparation of the hydrogen fumarate salt of Fesoterodine.

Further disclosed is the preparation of pharmaceutical formulations containing compounds of formula (I), such as Fesoterodine, and the preparation of pharmaceutical formulations containing a pharmaceutically acceptable salt of any of the compounds of formula (I), including, for example, the hydrogen fumarate or hydrochloride hydrate salts of Fesoterodine.

BACKGROUND

In man, normal urinary bladder contractions are mediated, in part, through cholinergic muscarinic receptor stimulation. Muscarinic receptors not only mediate, in part, normal bladder contractions, but may also mediate the main part of the contractions in the overactive bladder resulting in symptoms such as urinary frequency, urgency and urge urinary incontinence.

After administration of Fesoterodine and other phenolic monoesters of formula (I) to mammals, such as humans, these compounds are cleaved by esterases to form the Active Metabolite within the body. The Active Metabolite is known to be a potent and competitive muscarinic receptor antagonist (WO 94/11337). Fesoterodine and other phenolic esters of the formula (I) thus represent potential prodrugs for the Active Metabolite. Fesoterodine, in particular, has been shown to be an effective drug for the treatment of overactive bladder with symptoms of urge urinary incontinence, urgency, and urinary frequency, as well as detrusor hyperactivity (as described in U.S. Pat. No. 6,713,464 and EP-B-1,077,912).

A synthetic approach for the production of the Active Metabolite and monoesters of the phenolic hydroxy group of the Active Metabolite such as Fesoterodine has been described in U.S. Pat. No. 6,713,464 as follows:

In a first step, an ethereal solution is prepared from R-(−)-[3-(2-benzyloxy-5-bromophenyl)-3-phenylpropyl]-diisopropylamine, ethyl bromide and magnesium; this solution is diluted with dry THF and is cooled to −60° C.

In a second step, powdered solid carbon dioxide is added in small portions and the reaction mixture is warmed to room temperature.

In a third step, the reaction is quenched with an aqueous solution of ammonium chloride.

In a fourth step, the aqueous phase of the quenched reaction mixture is adjusted to a pH of 0.95.

In a fifth step, the pH adjusted aqueous phase is filtered and R-(−)-4-benzyloxy-3-(3-diisopropylamino-1-phenylpropyl)-benzoic acid hydrochloride can be recovered from the solid.

In a sixth step, the resulting purified benzoic acid is esterified to its corresponding methyl ester.

In a seventh step, the methyl ester of step six is reduced by the addition of lithium aluminium hydride. After a reaction for 18 hours, the reaction is quenched with water and the organic phase is dried over sodium sulphate, filtered and evaporated to dryness to gain the alcohol that gradually crystallized from an oil.

A diagram summarizing this multi-step synthesis is shown below.

Steps 1 to 5:

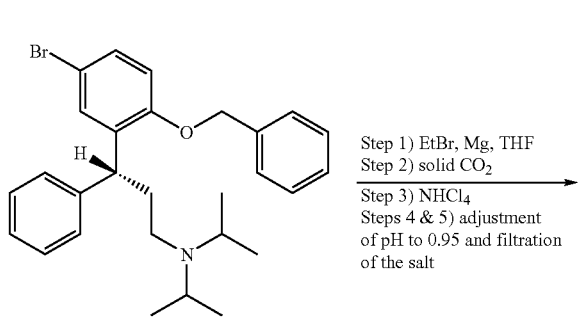

Step 1) EtBr, Mg, THF
Step 2) solid $CO_2$
Step 3) $NHCl_4$
Steps 4 & 5) adjustment of pH to 0.95 and filtration of the salt -continued

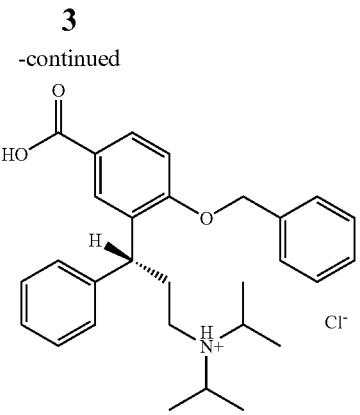

Step 6:

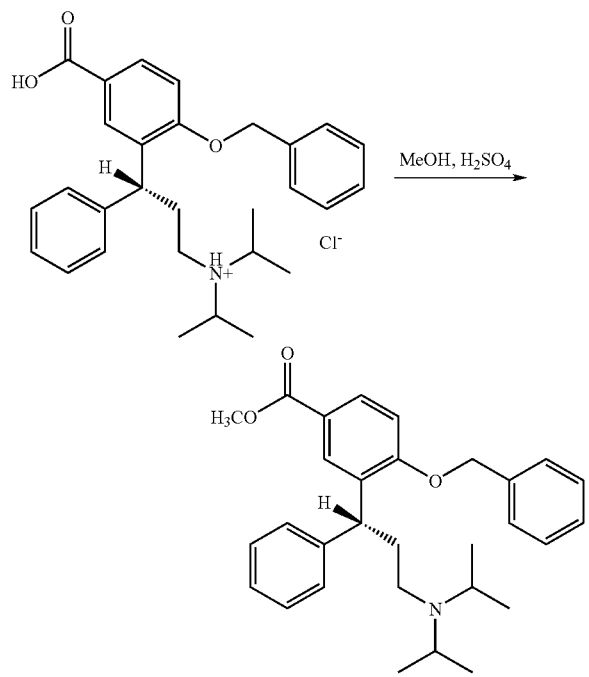

Step 7:

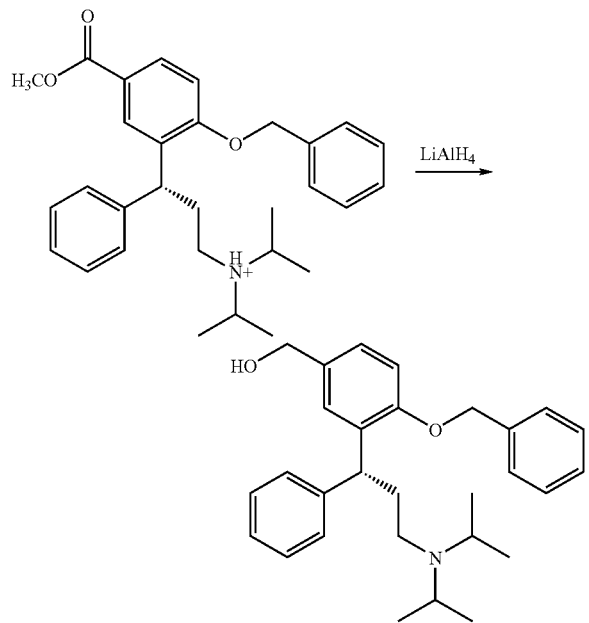

U.S. Pat. No. 6,713,464 further describes converting the methyl ester to the Active Metabolite, and then esterifying the Active Metabolite to a phenolic monoester, such as Fesoterodine.

WO 94/11337 also describes a multi-stage process to synthesize the precursor of the Active Metabolite.

These previously described methods for producing the Active Metabolite require numerous steps that result in complex purification procedures, time-delay, and enhanced possibility of human error, thereby prohibiting optimal efficiency and cost-effectiveness. Also, the solid carbon dioxide used in the art is difficult to handle on large scale due to the need to work at very low temperatures and to add the crushed dry ice portionwise, and due to the difficulties to control the very exothermic nature of the reaction. Also, the reduction step with lithium aluminium hydride used in the prior art causes a significant amount of waste on large scale, which is disadvantageous both from an economical as well as from an ecological point of view.

The present disclosure aims to overcome these problems and disadvantages. Surprisingly, it has now been found that the use of paraformaldyde or trioxane in the Grignard reaction using a Grignard initiator in the presence of an excess of Mg, is suitable to directly obtain a compound of formula (III) without previously synthesizing the corresponding ester. The use of paraformaldehyde or trioxane results in a shortened synthetic route to Fesoterodine via a compound of formula (III) by eliminating the production of the benzoic acid and the methyl ester intermediates and provides an increased overall yield.

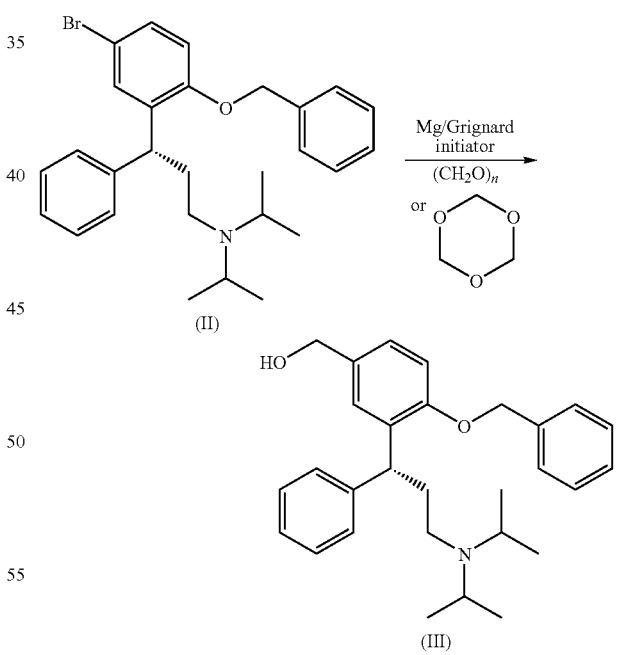

Accordingly, the use of paraformaldehyde or trioxane in the Grignard reaction initiated by the use of a Grignard initiator in the presence of extra Mg allows for a direct and more cost-effective synthetic approach to compounds of formula (I) via a compound of formula (III) thereby eliminating undesired side-products such as the benzoic acid derivatives, which often are formed when using an approach via the corresponding ester followed by a reduction step.

SUMMARY

Described herein is a shortened process for the preparation of compounds of formula (I):

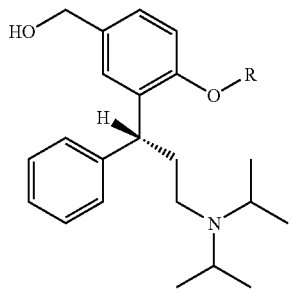

wherein R is hydrogen, a formyl group, a straight, branched or cyclic $C_1$-$C_6$ alkylcarbonyl group or a phenylcarbonyl group, including the Active Metabolite and its phenolic monoesters, such as Fesoterodine and its salts, and more particularly the hydrogen fumarate salt of Fesoterodine.

The shortened synthesis of compounds of formula (I) can be characterized by the following steps:

a) reacting a compound of formula (II)

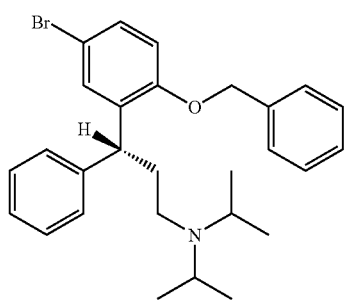

with a Grignard initiator and Mg, preferably in a solvent, to form a Grignard reagent,
b) optionally, reducing the temperature of the Grignard reagent to a lower temperature than in step a) and
c) reacting the Grignard reagent with paraformaldehyde or trioxane to obtain a compound of formula (III)

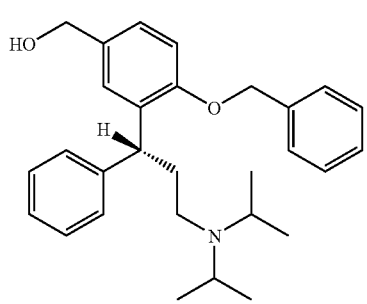

and then further reacting the compound of formula (III) in a known manner to obtain a compound of formula (I) and optionally salt formation.

Also described herein is a shortened process for the preparation of compounds of formula (I):

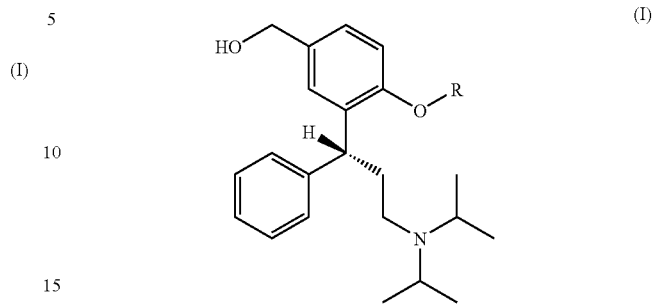

wherein R is hydrogen, formyl, a straight, branched or cyclic $C_1$-$C_6$ alkylcarbonyl group or a phenylcarbonyl group, including the Active Metabolite and its phenolic monoesters, such as Fesoterodine and its salts, and more particularly the hydrogen fumarate and hydrochloride hydrate salts of Fesoterodine, wherein said shortened process for the preparation of compounds of formula (I) can be characterized by the following steps:

a) combining a compound of formula (II):

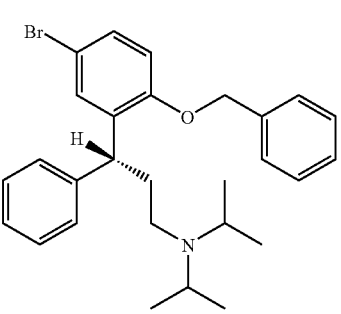

with MeMgCl and Mg in a solvent to form a reaction mixture,
b) optionally, reducing the temperature of the reaction mixture of step a) to a lower temperature than in step a) and
c) combining the reaction mixture of step a) with paraformaldehyde or trioxane, preferably paraformaldehyde, to obtain a compound of formula (III):

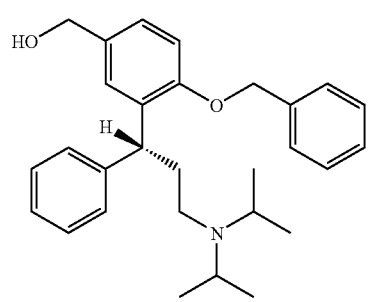

and then further reacting the compound of formula (III) in a known manner to obtain a compound of formula (I) and optionally salt formation.

DETAILED DESCRIPTION

The shortened synthesis via a Grignard reaction with a Grignard initiator, Mg and paraformaldehyde or trioxane which can be used in the preparation of the Active Metabolite and its phenolic monoesters of the type disclosed by formula (I), such as Fesoterodine, and more particularly Fesoterodine hydrogen fumarate, is now described in greater detail with reference to preferred embodiments.

In step a) of the process according to the present disclosure, a compound of formula (II)

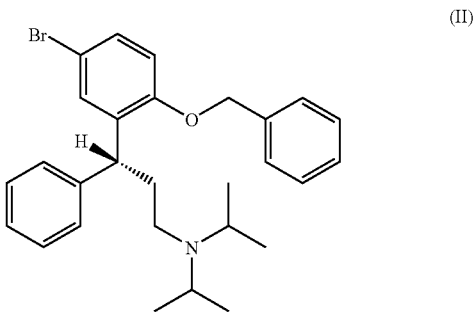

(II)

is reacted with a Grignard initiator in the presence of Mg in a solvent to form a Grignard reagent.

As used in this application, the term "Grignard initiator" refers to agents known in the art to start Grignard reactions. "Grignard initiators" comprise compounds of the general formula $R^1MgX$, or $R^1MgX/LiCl$ (see e.g. EP 1 582 523), wherein $R^1$ represents $C_1$-$C_{12}$ alkyl, $C_2$-$C_6$ alkenyl, $C_2$-$C_6$ alkynyl, substituted or unsubstituted phenyl or phenyl($C_1$-$C_6$) alkyl, wherein said phenyl may be substituted, e.g. with ($C_1$-$C_6$)alkyl, ($C_1$-$C_6$)alkoxy or $CF_3$; and wherein X is selected from bromide, chloride and iodide. $R^1$ is preferably selected from $C_1$-$C_6$ alkyl, vinyl, allyl, propenyl, ethynyl, phenyl or benzyl, and is more preferably $C_1$-$C_4$ alkyl.

Specific examples of Grignard initiators are iPrMgCl, iPrMgCl/LiCl, t-BuMgCl, t-BuMgCl/LiCl, MeMgCl/LiCl or, particularly preferably, MeMgCl.

The molar ratio of a Grignard initiator to Mg is preferably between about 1:2 and about 2:1, most preferably about 1:1, and the molar ratio of each of a Grignard initiator and Mg to the compound of formula (II) is preferably between about 1:1 and about 2:1, most preferably about 1:1 to about 1.5:1. If MeMgCl or a similar initiator is used in combination with LiCl, MeMgCl and LiCl are used in about equimolar amounts.

In a preferred embodiment, MeMgCl is used as a Grignard initiator. In an especially preferred embodiment, the molar ratio of MeMgCl to the compound of formula (II) is about 1:1 to about 1.5:1.

Preferably, step a) can be carried out by:
a1) dissolving a compound of formula (II) in a suitable solvent to form a solution, and
a2) adding said solution to a mixture of a Grignard initiator and Mg in a suitable solvent to form a Grignard reagent.

A preferred solvent for dissolving compound (II) in reaction step a1) is toluene, although other suitable solvents may be used. Preferably the water content in the solution containing compound (II) is not more than about 0.1 wt % and most preferably not more than about 0.05 wt %.

A preferred solvent for dissolving a Grignard initiator in reaction step a2) is THF, however other suitable ethers known to those skilled in the art may be used, including diethylether and t-butylmethylether.

The formation of the Grignard reagent as described in step a) is preferably carried out in a temperature range of about 40 to about 55° C. and most preferably in a temperature range of about 40 to about 50° C. The reaction can be conducted under agitation (e.g. stirring) up to completion.

In a preferred embodiment the Grignard can then be cooled down to ambient temperature, e.g. to about 20 to about 25° C. and held under anhydrous conditions, preferably with agitation, for the next steps of the process.

In step c) the resulting Grignard reagent is reacted with a suspension of paraformaldehyde or trioxane in THF to obtain the compound of formula (III) depicted below.

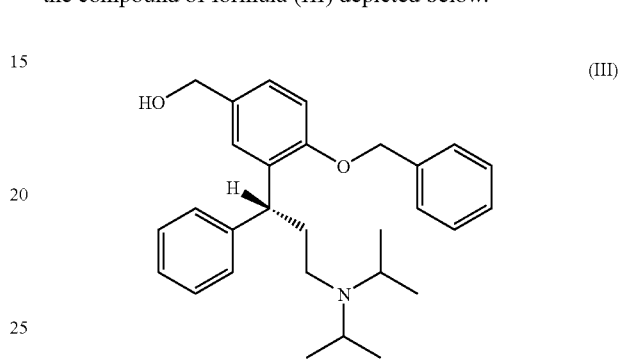

(III)

An excess of paraformaldehyde or trioxane as compared to a compound of formula (II) is preferred, with about 1.1-fold to about 50-fold excess of paraformaldehyde or trioxane, and an about 5 fold to about 50-fold excess being particularly preferable.

Paraformaldehyde is the most preferred reagent.

In one embodiment of the present invention, the reaction of the Grignard reagent with paraformaldehyde or trioxane, preferably with paraformaldehyde, is carried out at a temperature below room temperature, preferably below 10° C., under agitated conditions.

One option is to add the Grignard reagent slowly to paraformaldehyde or trioxane, optionally under stirring, to allow for a rapid and homogenous mixture of the reaction solution.

Another option is to add the paraformaldehyde or trioxane to the Grignard reagent, optionally under stirring, at ambient temperature until the reaction complete.

Step c) is completed by quenching the reaction mixture with a suitable quenching agent. A preferred quenching agent is aqueous ammonium chloride, although other quenching agents known to those skilled in the art may be used, including aqueous ethyl acetate, aqueous sodium chloride or aqueous hydrochloric acid solution.

Subsequently, a solvent exchange from the Grignard solvent (e.g. toluene and/or THF) to a suitable solvent for the hydrogenation (e.g. methanol) can be performed.

Suitable workup steps after the addition of the quenching reagent are e.g.
washing with water;
removal of water from organic phase e.g. by azeotropic drying;
solvent exchange to a solvent suitable for hydrogenation.
The process described above is disclosed in more detail in Example 1 of the experimental part of this application.

Another preferred embodiment of the present invention is a method for the preparation of a compound of formula (I) as defined above or of formula (Ib)

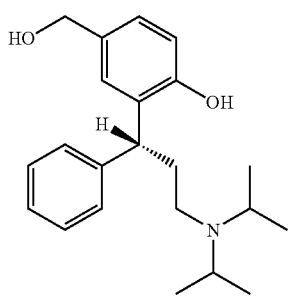

or a salt thereof, by first forming a compound of formula (III) as described above and then further reacting this compound in a suitable manner to form a compound of formula (I) or (Ib).

In a preferred embodiment, the compound of formula (III) can be further reacted with a debenzylation reagent to obtain a compound of formula (I) or (Ib), most preferably with Pd/C, H₂ in methanol.

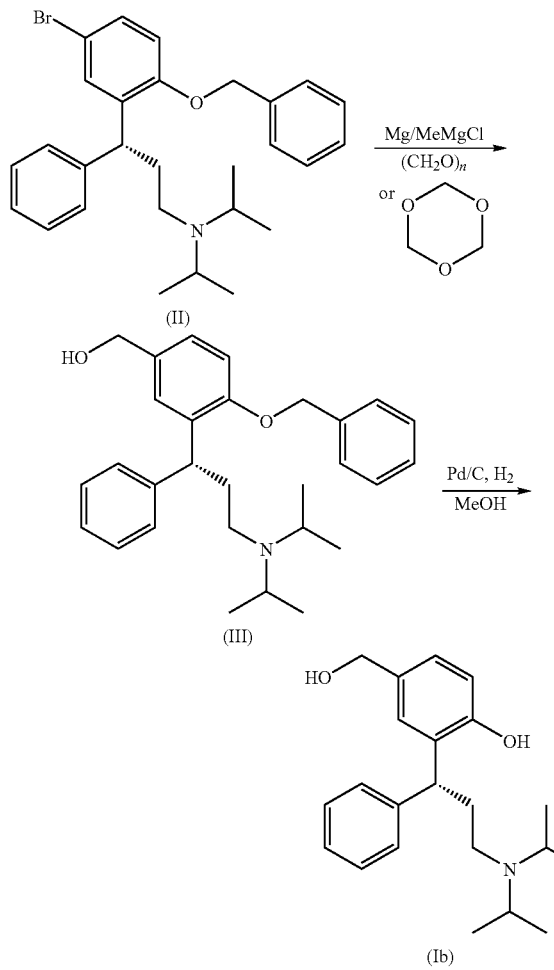

Following this reaction sequence, the compound of formula (Ib) can be isolated with a total yield of 46% over 2 steps. In contrast, the prior art synthesis according to in U.S. Pat. No. 6,713,464 and EP-B-1,077,912 has a reaction yield of (Ib) starting from (II) of about 26%.

A particularly preferred embodiment of the present invention is a process for the preparation of the Active Metabolite, and, if desired, its phenolic monoesters including Fesoterodine or a salt thereof, preferably a pharmaceutically acceptable salt of Fesoterodine, and most preferably the hydrogen fumarate salt of Fesoterodine, which process includes the steps of:

a1) dissolving the compound of formula (II) in a solvent, such as toluene, to form a reaction mixture, a2) adding said reaction mixture to a mixture of MeMgCl, Mg and THF to form a Grignard reagent, wherein the reaction can be performed at a reaction temperature of about 40 to about 50° C., b) optionally reducing the temperature of the Grignard reagent to a temperature below the temperature of step a2), and more preferably in the range of about 20 to about 25° C. and maintaining the Grignard reagent at the lower temperature, optionally under agitation, and c) reacting the resulting Grignard reagent with paraformaldehyde in a solvent (e.g. THF), preferably at a reaction temperature of below room temperature, most preferably at a reaction temperature of below 10° C., followed by quenching the thus obtained mixture with an aqueous ammonium chloride solution to obtain a compound of formula (III). Preferably an excess of paraformaldehyde is used, more preferably paraformaldehyde is employed in an excess of 1.1-fold to 50-fold, most preferably 5-fold to 50-fold excess. This compound can then be isolated or further processed as described above.

After formation of the compound of formula (III), one option is to further react the compound of formula (III) to obtain a compound of formula (I). This can be accomplished, for example, as follows:

d) debenzylating the protected alcohol to form the Active Metabolite mentioned above.

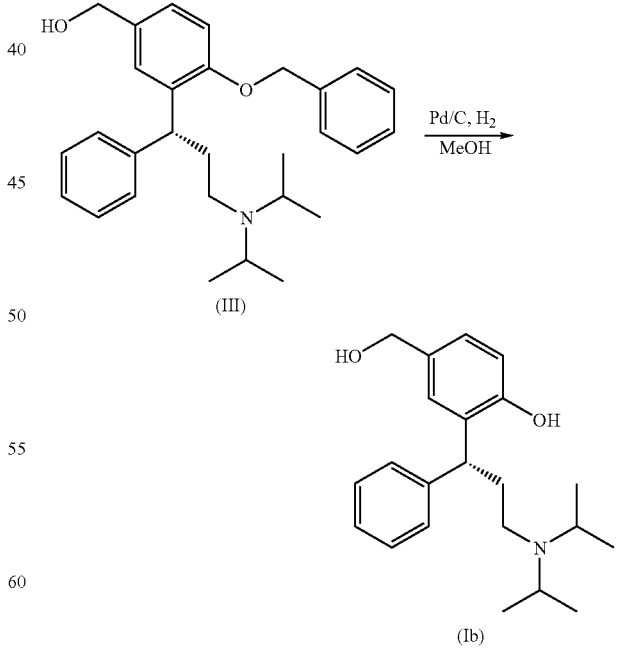

Another option is to convert the Active Metabolite to an ester thereof such as Fesoterodine or a salt of Fesoterodine, preferably the hydrogen fumarate salt of Fesoterodine, by:

e) phenolic monoacylation, and

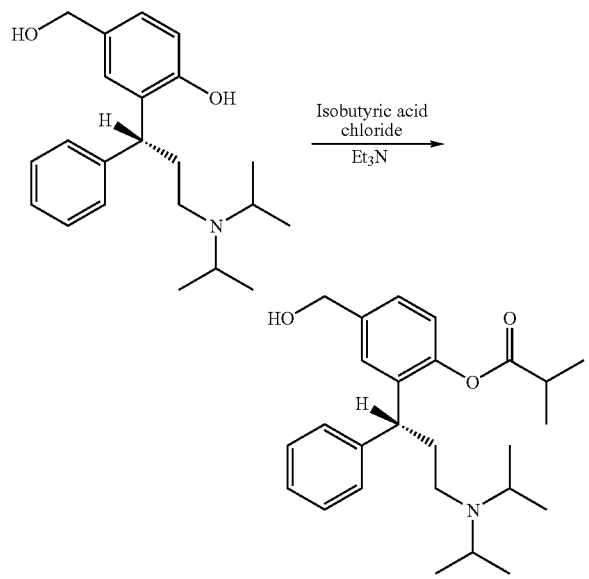

f) salt formation

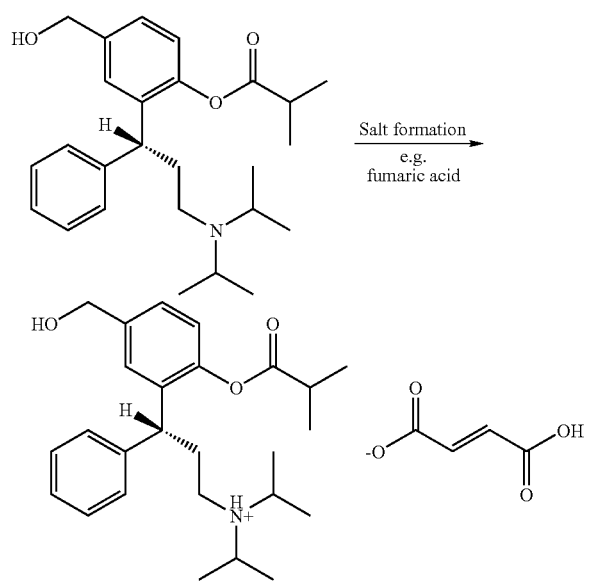

Examples of steps d) to f) are disclosed e.g. in U.S. Pat. No. 6,858,650.

The formation of other phenolic monoesters of the Active Metabolite is possible by using other organic acid halides in step e) of the above scheme.

The final compound (I) (phenolic monoesters of the Active Metabolite including Fesoterodine (Ia) or pharmaceutically acceptable salts thereof), and salts thereof, can then be formulated in a known manner to obtain a medicament that may be useful for e.g. oral, parenteral, or transdermal administration.

The present disclosure is further illustrated by the following non-exhaustive examples. The examples do not intend to limit the scope of this disclosure as defined in the claims below. The starting compound of formula (II) can be prepared in a known manner, e.g. such as described in the Experimental Part of U.S. Pat. No. 6,713,464.

EXAMPLES

Example 1

Preparation of R-(−)-4-Benzyloxy-3-(3-diisopropylamino-1-phenylpropyl)-phenyl methanol of formula (III)

(a) Stoichiometry MeMgCl:Mg: R-(−)-[3-(2-Benzyloxy-5-bromophenyl)-3-phenylpropyl]-diisopropylamine (formula II)=1:5:1:5:1.0

Magnesium turnings (2.25 g, 0.09 mol) and THF (150 ml) were charged to a 500 ml round bottomed flask with an agitator, dropping funnel, thermometer, nitrogen inlet and distillation apparatus applied. The system was purged with nitrogen and the mixture distilled to a target volume of 100 ml. The contents of the flask were cooled to 30° C. to 35° C. in a nitrogen atmosphere and methyl magnesium chloride (30.4 ml, 0.09 mol) was charged via a syringe to the flask. The mixture was aged for 1 hour at 30° C. The mixture was heated to reflux and the toluene solution of R-(−)[3-(2-Benzyloxy-5-bromophenyl)-3-phenylpropyl]-diisopropylamine (formula (II)) (50 ml, 0.06 mol) was charged dropwise via a pressure equalizing funnel to the reaction mixture. The reaction was agitated for 3 hours at which stage analysis indicated reaction completion (HPLC). Paraformaldehyde (9.05 g, 0.30 mol) and THF (200 ml) were charged to a 500 ml round bottomed flask with an agitator, dropping funnel, thermometer, nitrogen inlet and distillation apparatus applied.

The system was purged with nitrogen and the mixture distilled to a target volume of 100 ml. The mixture was cooled to 0° C. to 5° C. The reaction solution was charged to the paraformaldehyde and THF solution using a syringe maintaining the temperature below 10° C. while agitating. The resulting mixture was agitated for at least 1 hour. 10% ammonium chloride (75 ml) were charged to the reaction mixture and agitated for 2 hours. The biphasic mixture was transferred to a separating funnel and the lower aqueous layer was separated and the organic layer was washed with water (2×100 ml). The combined organic layers were dried azeotropically using a Dean Stark apparatus. The oily product was isolated by concentration in vacuum. The product was dissolved in methanol (400 ml) and to the resulting solution was charged 3.0 g of 5% w/w palladium on carbon (50% w/w water). The mixture was charged to a 2 L hydrogenation flask. The mixture is then agitated at 20 to 25° C. for 6 hours at a hydrogen pressure of 3.45-3.79 bar. The reaction mixture was charged from the reactor into a 1 L flask containing 40 ml of toluene and the reactor was washed with methanol (60 ml). The combined mixtures were filtered through a bed of Celite. This filterbed was washed with of methanol (60 ml). The combined filtrates were transferred to a 2 L flask equipped with an agitator, thermometer and distillation apparatus. The solvent was distilled maintaining a batch temperature below 25° C. under vacuum until a batch volume of 60 to 90 ml is obtained. Toluene (450 ml) was charged to the concentrated solution. The vacuum was reapplied and the batch was again distilled to a volume of 146 to 180 ml maintaining a batch temperature below 25° C. The batch is then further distilled until a batch volume of 46 to 60 ml is obtained maintaining a batch temperature below 45° C. Toluene (250 ml) was charged and the batch distilled to 25 ml to 30 ml. The mixture was allowed to cool to 20 to 25° C. and aged overnight. The resulting crystalline R-(−)-4-Benzyloxy-3-(3-diisopropylamino-1-phenylpropyl)-phenyl methanol (formula (III)) was filtered, washed with toluene (40 ml) and dried under vacuum at 40° C.

The invention claimed is:

1. A process for the preparation of a compound of formula (I)

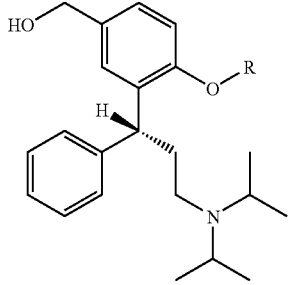

wherein R is hydrogen, a formyl group, a straight, branched or cyclic $C_1$-$C_6$ alkylcarbonyl group or a phenylcarbonyl group, or a salt thereof,
comprising:
a) reacting a compound of formula (II)

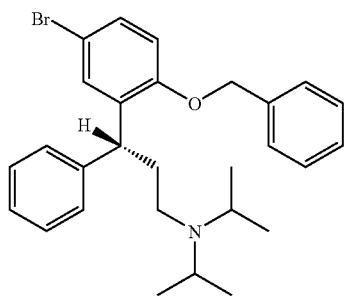

with a mixture of a Grignard initiator and Mg in a solvent to form a Grignard reagent,
b) reacting the Grignard reagent with paraformaldehyde or trioxane to obtain a compound of formula (III)

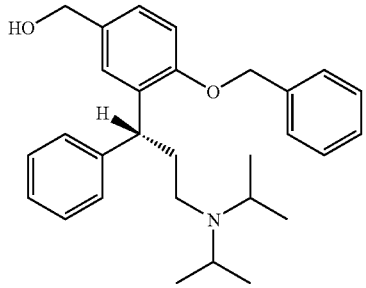

and then further reacting the compound of formula (III) to obtain a compound of formula (I).

2. The process of claim 1, wherein, prior to step b), the temperature of the Grignard reagent is reduced to a temperature below the temperature of step a).

3. The process of claim 1, wherein the obtained compound of formula (I) is converted into a salt.

4. The process of claim 1, wherein the compound of formula (I) is Fesoterodine having the formula (Ia)

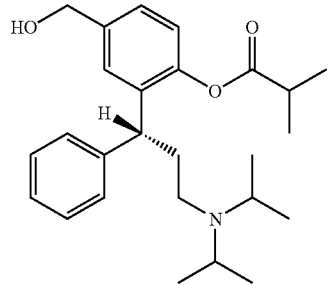

or a salt thereof.

5. The process of claim 1, wherein the compound of formula (I) is the hydrogen fumarate salt of Fesoterodine.

6. The process of any one of claim 1 or 5, wherein the Grignard initiator is a compound of the general formula $R^1MgX$ or $R^1MgX/LiCl$, wherein $R^1$ represents $C_1$-$C_{12}$ alkyl, $C_2$-$C_6$ alkenyl, $C_2$-$C_6$ alkynyl, substituted or unsubstituted phenyl or phenyl($C_1$-$C_6$)alkyl, and wherein X is selected from the group consisting of bromide, chloride and iodide.

7. The process of claim 6, wherein the Grignard initiator is selected from the group consisting of MeMgCl, MeMgCl/LiCl, t-BuMgCl/LiCl, and iPrMgCl/LiCl.

8. The process of claim 6, wherein the Grignard initiator is MeMgCl.

9. The process of claim 1, wherein paraformaldehyde is used in 1.1-fold to 50-fold molar excess compared to the compound of formula (II) in step b).

10. The process of claim 1, wherein a solvent is used in step b).

11. The process of claim 10, wherein the solvent is THF.

12. The process of any one of claim 1 or 5, wherein step b) is followed by quenching the reaction mixture with a suitable reagent.

13. The process of claim 12, wherein the reagent is aqueous $NH_4Cl$.

14. The process of any one of claim 1 or 5, wherein paraformaldehyde is reacted with the Grignard reagent in step b) to obtain a compound of formula (III).

15. The process of claim 1, wherein the molar ratio of the Grignard initiator to Mg is between 1:2 and 2:1, and the molar ratio of the Grignard initiator to the compound of formula (II) is between 1:1 and 2:1.

16. The process of claim 8, wherein the molar ratio of MeMgCl to Mg is between 1:2 and 2:1, and the molar ratio of MeMgCl to the compound of formula (II) is between 1:1 and 2:1.

17. The process of claim 1, wherein step a) is conducted by
a1) dissolving the compound of formula (II) in a suitable solvent to form a solution, and
a2) adding the solution to a Grignard initiator and Mg in a suitable solvent.

18. The process of claim 17, wherein the solvent in step a1) used for dissolving the compound of formula (II) is toluene and the solvent in step a2) is THF.

19. The process of claim 17, wherein
in step a1) the compound of formula (II) is dissolved in toluene,
in step a2) the solution is added to MeMgCl and Mg in THF and stirred up to the completion of the reaction,
before step b), the mixture as obtained in step a2) is maintained under stirring at a temperature below the temperature of the reaction of step a2),
in step b) the mixture is added to paraformaldehyde in THF, followed by adding a suitable quenching agent.

20. The process of claim 19, wherein the quenching agent is aqueous NH$_4$Cl.

21. The process of claim 1, wherein the reaction temperature of step a) is between 40 and 50° C.

22. The process of claim 2, wherein the temperature of the Grignard reagent is reduced to between 20 and 25° C.

23. The process of claim 1, wherein the reaction temperature of step b) is below 10° C.

24. The process of claim 1, wherein step b) is followed by a debenzylation step to obtain a compound of formula (Ib)

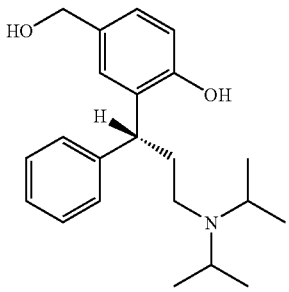

(Ib)

25. The process of claim 24, wherein the debenzylation step is conducted with Pd/C, H$_2$ in a suitable solvent.

26. The process of claim 25, wherein the solvent is methanol.

27. A process for the preparation of a pharmaceutical composition comprising Fesoterodine hydrogen fumarate comprising the steps of (i) preparing Fesoterodine hydrogen fumarate by the process of claim 5, and (ii) formulating the thus obtained Fesoterodine hydrogen fumarate to obtain a pharmaceutical composition comprising Fesoterodine hydrogen fumarate.

28. The process of claim 1, wherein the Grignard reagent is reacted with a suspension of paraformaldehyde or trioxane in step b).

* * * * *